United States Patent
Kepler et al.

(10) Patent No.: US 6,386,037 B1
(45) Date of Patent: May 14, 2002

(54) VOID DETECTOR FOR BURIED PIPELINES AND CONDUITS USING ACOUSTIC RESONANCE

(75) Inventors: William F. Kepler, Golden; Fred A. Travers, Lakewood, both of CO (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 0 days.

(21) Appl. No.: 09/874,236

(22) Filed: Jun. 6, 2001

(51) Int. Cl.[7] ............................................. G01N 29/00
(52) U.S. Cl. ........................... 73/579; 73/594; 73/599; 73/600; 73/602
(58) Field of Search .................. 73/579, 597, 598, 73/599, 600, 602, 11.01, 659, 632, 594, 623

(56) References Cited

U.S. PATENT DOCUMENTS

| | | | | |
|---|---|---|---|---|
| 4,428,235 A | * | 1/1984 | Sugiyama | 73/579 |
| 4,696,191 A | * | 9/1987 | Claytor et al. | 73/600 |
| 5,105,650 A | * | 4/1992 | Atkinson et al. | 73/594 |
| 5,144,838 A | * | 9/1992 | Tsuboi | 73/579 |
| 5,426,972 A | * | 6/1995 | Heirtzler et al. | 73/594 |
| 6,186,004 B1 | * | 2/2001 | Kaduchak et al. | 73/596 |
| 6,298,726 B1 | * | 10/2001 | Adachi et al. | 73/632 |
| 6,301,967 B1 | * | 10/2001 | Donskoy et al. | 73/579 |

* cited by examiner

Primary Examiner—Hezron Williams
Assistant Examiner—Jacques M. Saint-Surin
(74) Attorney, Agent, or Firm—Ross F. Hunt, Jr.

(57) ABSTRACT

A method and system are provided for detecting a void in backfill material such as soil surrounding a buried conduit such as a pipeline. The void is detected by monitoring an acoustic response from the conduit in response to acoustic excitation of the interior of the conduit. An analysis of changes in the acoustic response is then related to the presence or absence of a void in the backfill material.

20 Claims, 2 Drawing Sheets

VOID DETECTOR FOR BURIED PIPELINES AND CONDUITS USING ACOUSTIC RESONANCE

STATEMENT REGARDING FEDERALLY SPONSORED RESEARCH

This invention was made by employees of the United States Government and may be manufactured and used by or for the Government for governmental purposes without the payment of any royalties.

BACKGROUND OF THE INVENTION

1. Field of the Invention

The present invention relates to a method and system for detecting a void around a buried pipe or conduit, and in particular, a method and system for void detection using acoustic resonance.

2. Background of the Invention

Voids around a buried conduit (e.g., pipe) are gaps between the exterior surface of buried conduit walls and the backfill material covering the conduit. Voids surrounding a buried conduit may pose potential problems to the conduit and a system employing the conduit. For example, voids around pipelines allow water to flow therethrough which may lead to damage of the pipeline and associated systems. Therefore, it is advantageous to detect voids in an effort to avoid potential damage such as these and others.

Current systems for detecting voids around buried conduits include manual, visual inspection of the backfill material and the exterior of the conduit or a pipeline. One obvious major disadvantage of using visual inspection to detect voids around buried conduit is that various portions of the conduit may be inaccessible for visualization.

BRIEF SUMMARY OF THE INVENTION

In accordance with the present invention, a void in backfill material, such as soil surrounding a buried conduit may be detected from an acoustic frequency response of the conduit resulting from acoustic excitation of the conduit. By comparing the acoustic frequency response to a baseline frequency response range, a void is detected as an acoustic frequency response outside a baseline frequency.

According to one aspect of the invention, a method is provided for detecting a void outside a buried conduit. The method includes providing acoustic excitation of an interior portion of the conduit and detecting an acoustic frequency response of the conduit resulting from the acoustic excitation. The acoustic frequency response is compared to a baseline frequency response range. The void is identified when the acoustic frequency response is outside the baseline frequency response range.

According to another aspect of the invention, a system for detecting voids in backfill material around a buried conduit includes an acoustic exciter adapted for applying acoustic energy to an interior portion of the conduit. An acoustic frequency sensor detects a frequency response of the conduit resulting from the acoustic energy. A processor compares the acoustic frequency response to a baseline frequency response range and identifies the void as an acoustic frequency response outside the baseline frequency response range.

An advantage of the present invention relates to the use of detected resonant frequencies produced in a buried conduit in response to acoustic excitation to detect a void outside the buried conduit.

Another advantage of the present invention relates to the detection of a void outside a buried conduit where visual inspection of the void is not readily available or possible.

A further advantage of the present invention relates to determining the integrity of the backfill material surrounding a buried conduit. The present invention allows for the monitoring changes in acoustic frequency responses from a buried conduit resulting from applied acoustic excitation. As a result, integrity of the backfill material may be tracked as changes or variations in the acoustic frequency response.

Further features and advantages of the present invention will be set forth in, or apparent from, the detailed description of preferred embodiments thereof which follows.

DETAILED DESCRIPTION OF THE INVENTION

Figure 1A:
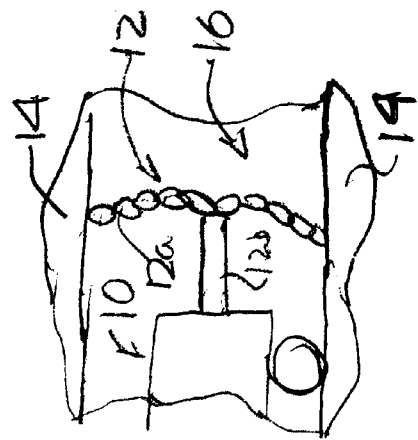
FIG. 1(a) is a view similar to FIG. 1, but broken away, depicting a further embodiment of the invention.

As indicated above, the present system employs the principle of resonance to detect voids in the backfill material outside the wall of a buried conduit such as a pipeline. A void may be detected from changes in the resonant frequency of the conduit and the decay time in response to the acoustic excitation.

A better understanding of the present invention can be gained by reference to the figures and associated descriptions thereof. Referring now to the drawings, and in particular to FIG. 1, illustratively depicted therein is a system for detecting a void in backfill material surrounding a buried conduit according to the present invention. In FIG. 1, the backfill material is denoted B and the void is denoted V.

The system includes a void detector device or detector 10 comprising an acoustic exciter 12 which applies acoustic energy to an interior wall portion 14 of the conduit 16 as the detector device 10 moves therealong. Void detector device 10 also includes acoustic frequency sensor 18 for detecting an acoustic frequency response to the applied acoustic energy.

Acoustic exciter 12 may comprise or include an impulse or pulser device (not shown) which generates an impulse and thus provides impulse excitation of conduit 16. For example, the impulse device may include a solenoid-operated hammer which physically impacts the interior wall. Alternatively, the impulse device may include piezoelectric elements employed to excite conduit 16 by impacting interior wall portion 14.

Figure 1:
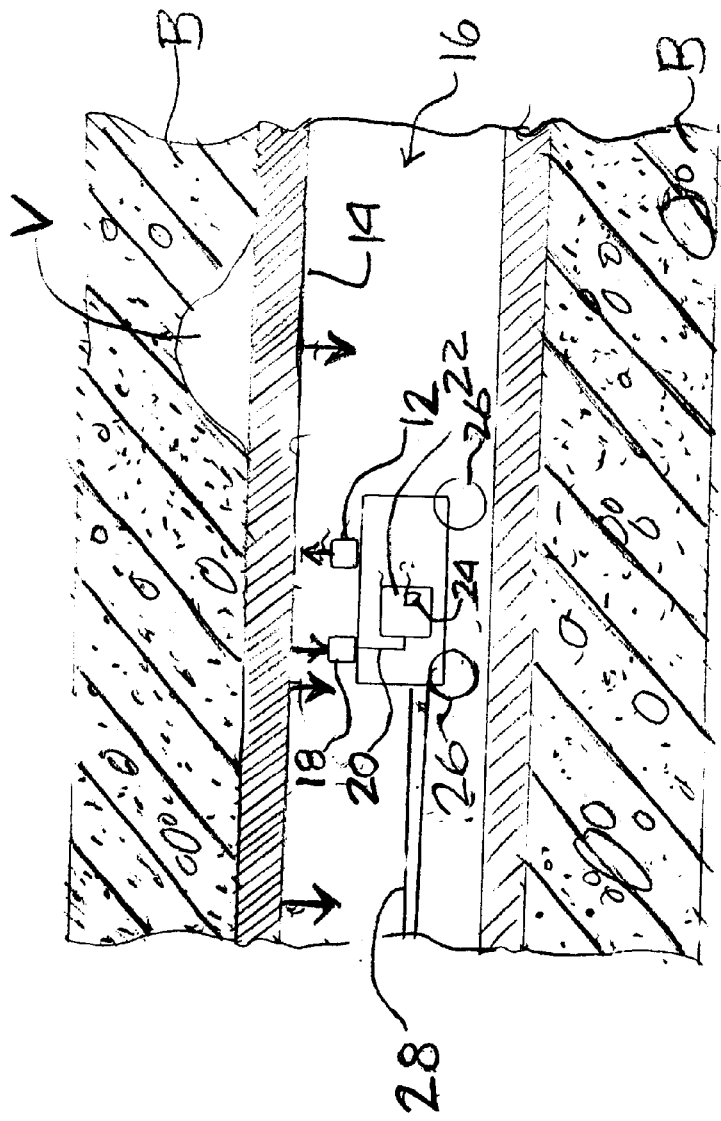
FIG. 1 is a highly schematic cross section view depicting a system for detecting a void in backfill material surrounding the outside of a buried conduit, according to a preferred embodiment of the present invention.

In a further alternative embodiment shown in FIG. 1a, acoustic exciter 12 includes a chain 12a mounted on a support member, or a similarly mounted wire brush (not shown), in physical contact with interior wall portion 14 which produces continuous excitation of conduit 16 through contact with wall 14 as void detector device 10 traverses through conduit 16.

In yet an alternative form (not shown), acoustic exciter 12 may include a wide band white noise sound generator (not shown) for producing high sound pressure levels. The sound produced is directed to the interior portion 14 of wall 16 thereby eliciting a resultant frequency response.

Acoustic frequency sensor 18 may comprise either an acoustic sensor or a mechanical sensor and, for example, acoustic sensor 18 may comprise a microphone which detects an acoustic frequency response.

In alternative embodiments, acoustic frequency sensor 18 may include an accelerometer, strain gage, optical displacement/vibration sensor, and eddy current displacement sensor as well as other types of displacement/vibration sensors or detectors known in the art.

Acoustic frequency sensor 18 is connected by a connector 20 to a microprocessor 22 and, in a preferred embodiment, produces an output signal by converting the mechanical vibration component of the acoustic frequency response into a corresponding electrical output signal. This output signal may be stored in a memory 24 of microprocessor 22.

Processor 22 analyses the electrical output signal using a mathematical algorithm to analyze the spectral content and the decay time of the acoustic frequency response. Further, processor 22 compares the spectral content and the decay time of the acoustic frequency response to a baseline frequency response. The baseline frequency response corresponds to a previously acquired acoustic frequency response for a known "good" area of conduit 16 such as in an area of interior wall portion 14 upstream of void. As will be apparent, the baseline value generated is unique for each conduit system.

Void detecting device 10 also includes wheels 26 which allow void detecting device 10 to traverse conduit 16. An umbilical cord 28 provides electrical connections for power, control signals and a data link. During operation, void detecting device 10 proceeds through conduit 16 while directing acoustic excitation to the interior wall 14 of conduit 16. As a result of this excitation, conduit 16 produces resonant vibrations which are detectable by acoustic frequency sensor 18.

The resonant frequency changes depending upon the density (e.g., compactness) of the backfill material B that surrounds buried conduit 16. It will be understood that the acoustic frequency response resulting from acoustic excitation of the interior conduit wall portion 14 in an area where there is no void is different than acoustic frequency response resulting from acoustic excitation of the interior wall portion 14 adjacent to void. Using this basic principle, void V can be identified by processor 22 from the acoustic frequency response.

Figure 2:
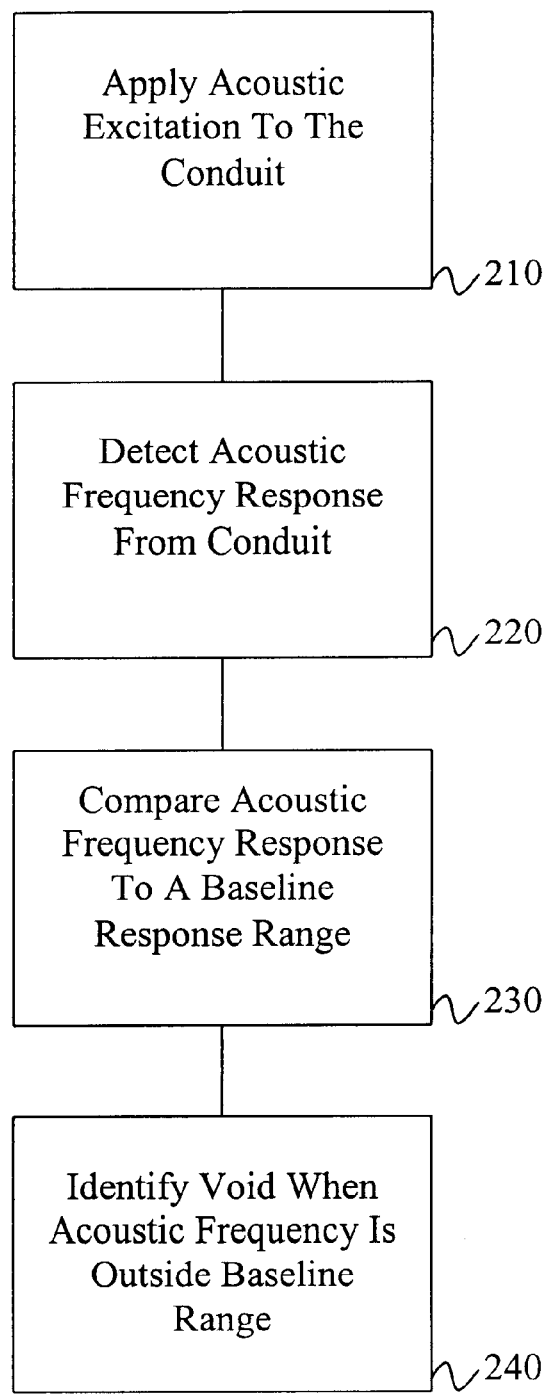
FIG. 2 is a flow diagram depicting a preferred method according to the present invention.

To further illustrate the operation of void detecting device 10 and to aid in providing a better understanding of the present invention, reference is made to FIG. 2 which is a flow diagram depicting a preferred method of operation for detecting voids in the backfill material B which surrounds conduit 16. This preferred method employs the principle of resonance to detect voids, such as void V, in the wall of a buried conduit 16, i.e., the presence of void V is detected from changes in the resonant frequency and changes in the time delay of an acoustic frequency response produced in response to acoustic excitation provided by acoustic exciter 12.

The operation of the system is predicated on the fact that when a conduit structure is acoustically excited by an external stimulus, the structure will respond by vibrating at its resonant frequencies and harmonics thereof. First, a baseline frequency response range of the conduit structure is determined experimentally in a known area of well-compacted, homogenous backfill material. After the baseline frequency response range has been established, unknown areas are tested. Deviations from (i.e., falling outside of) the baseline frequency response range indicate deficiencies in the backfill material.

Referring now specifically to FIG. 2, along with FIG. 1, acoustic exciter 12 applies acoustic excitation to the interior surface 14 of conduit 16 (block or step 210 in FIG. 2). As indicated above, the acoustic excitation may be in the form of an impulse excitation in which acoustic exciter 12 repeatedly strikes the interior surface 14 of conduit 16 as void detecting device 10 traverses through conduit 16.

Alternatively, rather than pulsed excitation, acoustic excitation may be generated continuously along an interior portion 14 of conduit 16 by moving a chain 12a as shown in FIG. 1a, or wire brush (not shown), along interior surface 14 of conduit 16 as void detecting device 10 traverses through conduit 16. As was described above, in yet another embodiment, acoustic excitation of conduit 16 may be produced by acoustic excitation in the form of a wide band white noise sound directed to interior wall surface 14 of conduit 16.

Preferably, regardless of the form of acoustic excitation used, it is advantageous to use a high energy excitation source. However, response processing algorithms may be adapted to also permit lower energy excitation sources to be used effectively.

Conduit 16 produces an acoustic frequency response as a result of acoustic excitation. The acoustic frequency response is detected by acoustic frequency sensor 18 (block or step 220 of FIG. 2). The acoustic frequency response is converted into an output signal by acoustic frequency sensor 18.

As will become evident to one of ordinary skill, the preferred method by which acoustic frequency response is detected depends upon the composition of conduit 16 and the method in which acoustic excitation is generated.

The acoustic frequency response may be detected acoustically and mechanically. For example, in the case of impact excitation, the frequency of response is readily measured acoustically using a microphone. In addition, as indicated above, other sensing or measuring devices that can be used include accelerometers, strain gages, optical displacement/vibration sensors, eddy current displacement sensors and other types of displacement/vibration detector or sensors known in the art.

As indicated by block 230, in the next step, the acoustic frequency response is compared to a baseline frequency response range. A baseline frequency response range is empirically derived by using the present method on a portion of conduit 16 in a known "good" area (i.e., where backfill B is well-compacted and homogeneous). As is apparent, the baseline value is unique for every conduit system.

During an initial calibration, a baseline frequency response is established by first obtaining several response signals in the known good area of the conduit. The frequency response signals are analyzed to determine whether the frequency response signals fall statistically within the same response range, i.e., outlying response signals are not used in computing the baseline frequency response range. Anomalies in conduit 16, such as bends, joints, access panels or hatches should be avoided in determining the baseline response.

The output signal is analyzed and spectral content and a decay time component of the acoustic frequency response are separated out. The spectral response is qualified by determining the frequency of the spectral peaks as well as the relative magnitude of these peaks. Also, the time domain signal is analyzed for the decay time of the acoustic frequency response.

In good areas of conduit 16, a statistical variation (i.e., range) is determined for each of the measured parameters. Outside of the known good areas, significant deviation from the established baseline are considered to indicate anomalies in the backfill material, i.e., anomalies such as void V.

Specifically, as indicated by block or step 240, void V is identified when the acoustic frequency response is outside a baseline range. For example, for the acoustic frequency response produced from acoustic excitation of a "good" portion of interior conduit wall, the spectral response and decay time of the acoustic frequency response are compared to a baseline range by processor 22. Processor 22 compares the spectral response and decay time of the current acoustic frequency response to a baseline range and, in the area of void V, would determine that the acoustic frequency response is outside of the baseline frequency response range. Consequently, processor 22 is able to identify void V.

Although the invention has been described above in relation to preferred embodiments thereof, it will be understood by those skilled in the art that variations and modifications can be effected in these preferred embodiments without departing from the scope and spirit of the invention.

What is claimed is:

1. A method for detecting a void in backfill material around a buried conduit, said method comprising the steps of:
    providing acoustic excitation of an interior portion of the conduit;
    detecting an acoustic frequency response of the conduit resulting from the acoustic excitation;
    comparing the acoustic frequency response to a baseline frequency response range; and
    identifying the void in backfill material when the acoustic frequency response lies outside the baseline frequency response range.

2. The method of claim 1, wherein said step of providing acoustic excitation comprises introducing an impulse excitation to the conduit.

3. The method of claim 2, wherein the impulse excitation is generated by impacting the interior portion of the conduit using an impacting device.

4. The method of claim 1, wherein said step of providing acoustic excitation comprises generating a wide band white noise sound.

5. The method of claim 1, wherein said step of providing acoustic excitation comprises the step of producing continuous excitation by directing acoustic excitation along a segment of the conduit.

6. The method of claim 1, wherein said step of detecting the acoustic frequency response comprises using an acoustic sensor to detect the acoustic frequency response.

7. The method of claim 6, wherein the acoustic sensor comprises a microphone.

8. The method of claim 1, wherein said step of detecting the acoustic frequency response comprises using a mechanical sensor to detect the acoustic frequency response.

9. The method of claim 1, wherein said step of detecting the acoustic frequency response comprises using one of an accelerometer, a strain gage, an optical displacement/vibration sensor, and an eddy current displacement sensor to detect the acoustic frequency response.

10. The method of claim 1, wherein the frequency response comprises a resonant frequency and a decay time.

11. A system for detecting voids in backfill material around a buried conduit, said system comprising:
    an acoustic exciter adapted for applying acoustic energy to an interior portion of the conduit;
    an acoustic frequency sensor for detecting a frequency response of the conduit resulting from the acoustic energy; and
    a processor for comparing the acoustic frequency response to a baseline frequency response range and for identifying the voids in backfill material as an acoustic frequency response outside the baseline frequency response range.

12. The system of claim 11, wherein said acoustic exciter comprises an impulse device operable to impact the interior portion of the conduit thereby generating the acoustic energy.

13. The system of claim 11, wherein said acoustic exciter comprises a translatable device operable to be in physical contact with the interior portion of the conduit and to produce continuous excitation when translated across the interior portion of the conduit.

14. The system of claim 13, wherein said translatable device comprises a chain.

15. The system of claim 11, wherein the acoustic exciter comprises a wide band white noise sound generator.

16. The system of claim 11, wherein said acoustic frequency sensor comprises an acoustic sensor for detecting the acoustic frequency response.

17. The system of claim 16, wherein said acoustic sensor comprises a microphone.

18. The system claim 11, wherein said acoustic frequency sensor comprises a mechanical sensor for detecting the acoustic frequency response.

19. The system of claim 11, wherein said acoustic frequency sensor comprises one of an accelerometer, strain gage, optical displacement/vibration sensor, and eddy current displacement sensor.

20. The system of claim 11, wherein the frequency response comprises a resonant frequency component and a decay time component.

* * * * *